United States Patent [19]

Howson

[11] 4,082,087
[45] Apr. 4, 1978

[54] BODY CONTACT ELECTRODE STRUCTURE FOR DERIVING ELECTRICAL SIGNALS DUE TO PHYSIOLOGICAL ACTIVITY

[75] Inventor: David C. Howson, Trumansburg, N.Y.

[73] Assignee: Isis Medical Instruments, Minneapolis, Minn.

[21] Appl. No.: 766,836

[22] Filed: Feb. 7, 1977

[51] Int. Cl.² ............................................. A61B 5/04
[52] U.S. Cl. ......................... 128/2.06 E; 128/2.1 E; 128/417; 128/DIG. 4
[58] Field of Search ............ 128/2.06 E, 2.1 E, 2.1 Z, 128/303.13, 404, 405, 406, 410, 411, 416, 417, 418

[56] References Cited

U.S. PATENT DOCUMENTS

| | | | |
|---|---|---|---|
| 2,590,876 | 4/1952 | Landauer | 128/417 |
| 3,387,608 | 6/1968 | Figar | 128/2.06 E |
| 3,420,223 | 1/1969 | Day et al. | 128/2.06 E |
| 3,472,233 | 10/1969 | Sarbacher | 128/417 X |
| 3,572,322 | 3/1971 | Wade | 128/2.06 E |
| 3,587,565 | 6/1971 | Tatoien | 128/2.06 E |
| 3,606,881 | 9/1971 | Woodson | 128/2.06 E |
| 3,741,219 | 6/1973 | Sessions | 128/417 |
| 3,750,649 | 8/1973 | Severingheus | 128/2.1 Z |

FOREIGN PATENT DOCUMENTS

| | | | |
|---|---|---|---|
| 394,385 | 4/1924 | Germany | 128/416 |
| 264,608 | 6/1970 | U.S.S.R. | 128/2.1 E |

Primary Examiner—Robert W. Michell
Assistant Examiner—Lee S. Cohen
Attorney, Agent, or Firm—Martin Lu Kacher

[57] ABSTRACT

An electrode structure for use with medical electronics instruments such as electromyographs is described. A thin, flexible body of non-conductive material has one or more wells therein. A flexible conductive member which provides an electrode is disposed at the bottom of each well. The spacing between a plurality of electrodes, which can provide bipolar and ground inputs to the medical electronic instrument, is precisely determined by virtue of the disposition of the electrodes in the wells. The electrode structure provides contact with a body surface, usually the skin. To facilitate the contact a conductive jelly is used. This conductive jelly is received in the wells. It makes contact with the electrodes. Ribs are provided in the regions between the electrodes which form a seal at the skin so as to prevent the flow of conductive fluid between electrodes; thus preventing short circuits. The flexibility of the structure provides for comfort and reliable long term attachment and also for maintaining the contact of the electrodes and sealing ribs with the skin as the skin and muscle beneath, flex.

11 Claims, 8 Drawing Figures

BODY CONTACT ELECTRODE STRUCTURE FOR DERIVING ELECTRICAL SIGNALS DUE TO PHYSIOLOGICAL ACTIVITY

The present invention relates to an electrode structure for deriving electrical signals due to physiological activity and particularly to an electrode structure for deriving electrical signals appearing at the surface of the body of a patient, as when placed in contact with the skin.

The invention is especially suitable for use with electromyographic apparatus, sometimes referred to as biofeedback apparatus which senses electrical activity of muscles. Such apparatus is used in the rehabilitation of many neuromuscular deficits as may result from strokes, cerebral palsy, spasticity, tendon and nerve transplants and the like, as well as for diagnostic purposes. The electrode structure provided by the invention can however be used to derive or sense signals representing other physiological activity such as electrocardiographic and electroencephalographic signals.

Deriving signals representing physiological activity has been particularly difficult in that the signals are of low amplitude such that they can easily be distorted or buried in noise. It has been suggested to use indwelling electrodes for deriving such signals. For example, in electromyographic apparatus, insulated wires introduced, as by hypodermic needles, have been used to derive the necessary signals. Various forms of electrodes have been attempted. For example, flat plates have been taped to the surface of the skin. Reference may be had to U.S. Pat. No. 2,712,975, issued July 12, 1955 for further information regarding such electrodes and electrode structures.

It has been found in accordance with the invention that electrical signals substantially free of noise and distortion can be derived from the body's surface, as from the skin, by an electrode structure whereby several electrodes can be maintained in precise spaced relationship with the skin while maintaining good electrical contact without short circuits therebetween. The small fixed electrode spacing provides for maximum sensitivity and selectivity especially with small muscles as those in the hand, face and neck.

Briefly described, the electrode structure uses a body of flexible non-conductive material such as a polymeric material which can be formed to shape in a mold. One or more blind holes is molded into the body on the face thereof which is to be placed in contact with the skin. At the bottom of each of these holes there is placed a flexible conductive member which forms an electrode. Leads may be connected to the electrodes and brought out from the flexible body to the instrument which handles the signals. The blind holes form wells. The electrodes are precisely disposed with respect to each other since they may be fixed in position during the molding process. The electrode structure can be used with a conductive jelly. The jelly is placed in the wells or on the skin and forms an elastic bridge between the electrodes and the skin, thus providing a constant low resistance path even when the skin and the flexible body and electrodes flex. The flow or migration of the jelly, while the electrode structure is in place on the skin, is counteracted by means of ribs or ridges which are formed in the regions between the wells. These ribs provide seals at the skin when the electrode structure is placed upon the skin. One or more of these ribs may be used and the ribs may surround the wells in whole or in part. The ribs may be formed integrally with the body of flexible non-conductive material during the molding process. In order to secure the electrode structure to the body, as for example on the arm or on the hand, surgical tape may be used. Alternately a tacky material may be coated on the face of the electrode structure which is adapted to be placed in contact with the skin, or double sided surgical tape may be used.

In electromyography as signals are derived by placement of electrodes such that they are spaced from each other along, or otherwise with respect to the muscle fiber, a change in the placement of the electrode results in noise and distortion of the signal. Accordingly, precise placement obtained through the use of an electrode structure embodying the invention is especially advantageous when used with electromyograph instruments. This precise placement or spacing of the electrodes is provided in a small, thin, flexible structure which maintains contact of the electrodes and ribs with the skin as well as provides for comfort and reliable long term attachment.

Accordingly, it is an object of this invention to provide improved electrode structures for use in deriving signals due to physiological activity.

It is another object of the present invention to provide an improved multiple contact electrode structure for deriving a plurality of inputs to instruments which handle such signals.

It is a still further object of the present invention to provide a flexible electrode structure which can be placed in contact with the skin without discomfort to a patient.

It is a still further object of the present invention to provide an improved electrode structure which affords precise electrode separation while acquiring signals due to physiological activity.

The foregoing and other objects and advantages of the invention as well as presently preferred embodiments thereof will become more apparent from a reading of the following specification in connection with the accompanying drawings in which.

Figure 1:
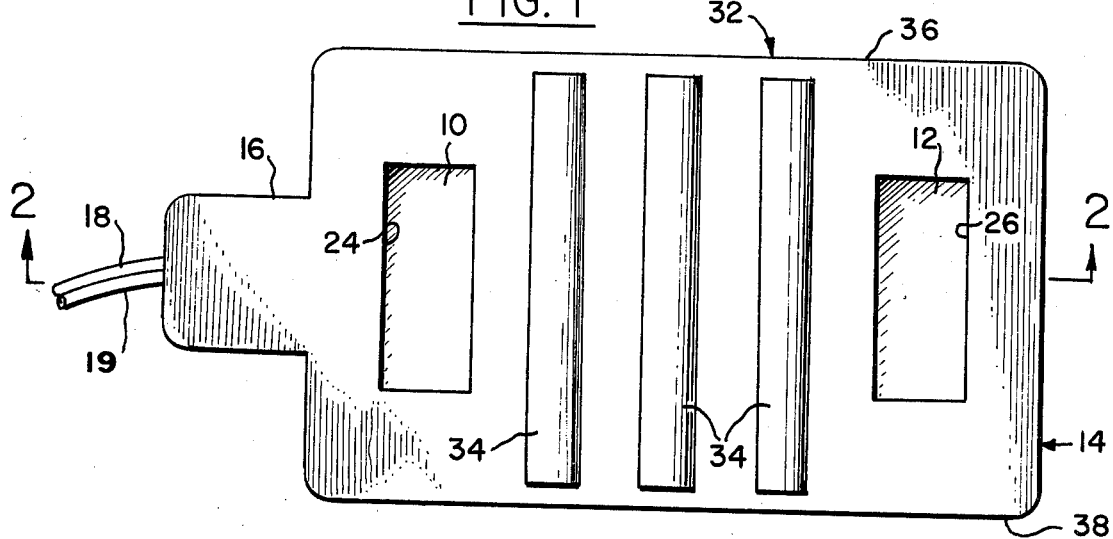
FIG. 1 is a plan view of an electrode structure in accordance with an embodiment of the invention.
Figure 2:
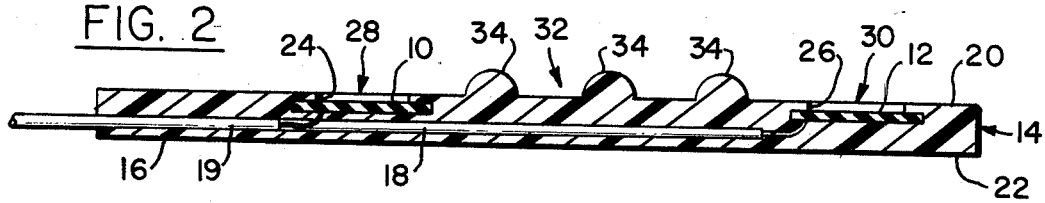
FIG. 2 is a sectional view of the electrode structure as shown in FIG. 1, taken along the line 2—2 in FIG. 1.

Referring more particularly to FIGS. 1 and 2. There is shown an electrode structure containing a pair of electrode members 10 and 12. These members are preferably platelets of flexible conductive material. It is preferred to use a so-called conductive rubber. Conductive rubber is a polymeric material containing conductive particles, preferably silver particles (polymeric materials are colloquially known as plastics). A suitable conductive rubber is sold in sheet form by Emerson & Cuming Co. of Canton, Mass, under their trade name ECCOSHIELD SV-R, which is known generically as conductive silicone rubber. This material is soft and elastic. The precise placement of the electrodes 10 and 12 in contact with a body surface such as the skin of a patient, is obtained in the electrode structure through the use of a generally rectangular body of flexible non-conductive material 14. This material is preferably a polymeric material which may be molded and cured either by air drying or under heat. Silicone and natural rubber and polyurethane are suitable materials for the body 14. This material is also soft and elastic. Silicone rubber is presently the preferred material. Such material is sold under the trade name SYLGARD 187 by Dow Corning Corp., of Midland, Mich. An end 16 of the body 14 is reduced. It is from this end 16 that conductors 18 and 19 emanate from the body 14. The conductors 18 and 19 may be insulated wires which are connected to the rectangular platelets which serve as the electrode members 10 and 12. The conductors 18 and 19 may be assembled to a connector or plug. The connector or plug is received in the medical electronic instrument, such as the electromyograph or biofeedback apparatus with which the electrode structure is used.

The body of flexible non-conductive material 14 has opposite faces 20, 22. The face 20 is adapted to be disposed in contact with the patient's skin when the electrode structure is placed in operation.

A pair of blind holes 24 and 26 extend into the body 14 from the face 20. These holes are rectangular in shape but smaller in size than the electrode members 10 and 12. The electrode members 10 and 12 are disposed at the bottom of wells 28 and 30. These wells are spaced from each other longitudinally of the body 14. Between the wells 28 and 30 there is a region 32 of the body 14 which separates the wells and keeps the electrodes 10 and 12 insulated from each other. In this region 32, and extending laterally across the body, are one or more ribs 34. Three ribs 34 are used in the electrode structure shown in FIGS. 1 and 2. They are parallel to each other and are equally spaced between the wells 28 and 30. The ribs 34 are longer than the wells and the ribs extend almost to the longitudinal edges 36 and 38 of the body 14.

The electrode structure is preferably provided as an integral device which is formed by molding. The ribs 34 are formed together with the body 14 as the polymeric material solidifies in the mold. The wells 28 and 30 may be formed by posts in the mold. The electrodes 10 and 12 are placed on these posts, together with the conductors 18 and 19. The polymeric material (such as the silicone rubber resin above mentioned) is then placed in the mold. When the material hardens, as by catalytic polymerization in the case of the silicone rubber resin, the electrode structure is formed. It remains only to remove any flash which is attached to the extremes of the body 14.

In use, the electrode structure is disposed on the skin of the patient, such as upon his forearm or upon his hand, in the region where signals corresponding to electrical activity are present. It is desirable to use conductive jelly so as to provide better contact between the electrodes 10 and 12 and the skin. To this end conductive jelly may be placed on the skin in the area where contact is to be made or in the wells 28 and 30. Any suitable conductive jelly (sometimes called an aqueous electromedial coupling agent) such as sold under the trade name LECTRON II by Pharmaceutical Innovations Inc., of Newark, N.J., and which is commercially available, may be used.

The electrode structure is placed on the skin and the face 20 is pressed against the skin. The electrode structure may be taped in place by adhesive tape, or alternatively a tacky material may be placed on the face 20 so that the electrode structure is self-adhering. Contact between the electrodes 10 and 12 and the skin of the patient is caused by the deflection of the electrode structure as it conforms to the skin of the patient and is assured by reason of the conductive jelly in the wells 28 and 30. The jelly forms an elastic bridge between the electrodes and the skin and provides a constant low resistance path therebetween. The ribs 34 contact the skin and serve as seals. The flow of conductive jelly, or even of body secretions which may be conductive, is prevented by the seals formed by the ribs 34. Accordingly, the short circuits between the electrodes 10 and 12 is substantially eliminated.

The electrode structure of FIGS. 1 and 2 may suitably be very thin, say 0.06 inch thick as measured between the top of the ribs 34 and the face 22. The rectangular body, except for the end 16 may suitably have a length of approximately one inch and a width of approximately one-half inch.

Figure 3:
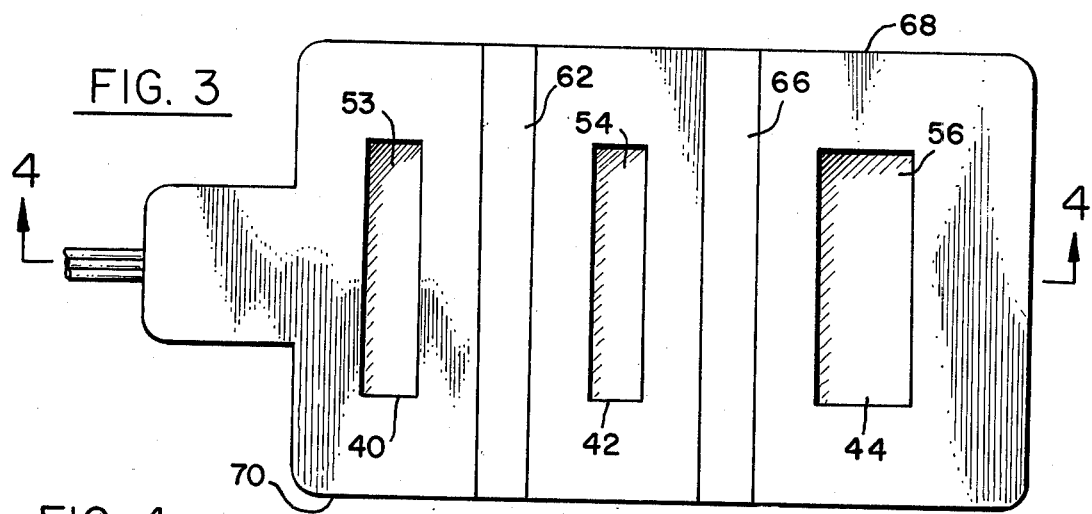
FIG. 3 is a plan view of an electrode structure in accordance with another embodiment of the invention.
Figure 4:
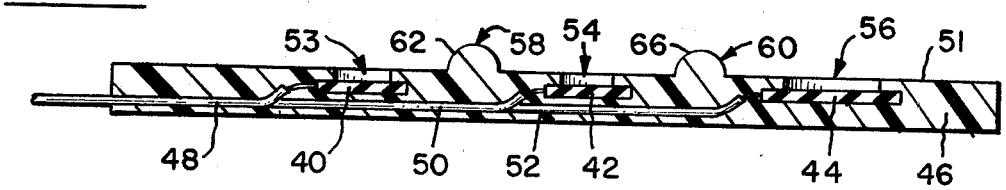
FIG. 4 is a sectional view of the structure shown in FIG. 3 taken along the line 4—4 in FIG. 3.

Referring to FIGS. 3 and 4, there is shown another electrode structure embodying the invention. This structure has three electrodes 40, 42 and 44. Each electrode may be a flexible rectangular platelet of the same type of material as used for the electrodes 10 and 12 (FIGS. 1 and 2). The electrode 44 may be somewhate wider. This electrode 44 may be used as a connection to ground in the instrument with which the electrode structure is used. The electrode 44 may be used to provide a d.c. return (leakage) path for the amplifier input. Ground may either be at zero or some reference potential. The other two electrodes 40 and 42 may be used to provide bipolar inputs to a differential or balanced amplifier at the input of the instrument. The reference voltage also controls common mode inputs to the differential amplifier, thereby reducing introduction of noise and other spurious signals. The position of the reference electrode 44 with respect to the bipolar input electrodes 40 and 42 can be precisely maintained in the electrode structure. The electrodes 40, 42 and 44 are disposed within a body 46 of flexible non-conductive material as by being molded integrally therewith by the process explained in connection with FIGS. 1 and 2.

Each of the electrodes 40, 42 and 44 has a separate conductor 48, 50 and 52. These are insulated wires connected to the electrode platelets 40, 42 and 44.

The surface 50 of the body 46 which is adapted to be disposed in contact with the body surface (viz. the skin) of the patient is provided with wells 53, 54 and 56 at the bottoms of which the electrodes 40, 42 and 44 are disposed. The regions 58 and 60 between adjacent pairs of the electrodes 40, 42 and 44 are provided with ribs 62 and 66. These ribs extend laterally across the regions and are coterminous with the longitudinal edges 68 and 70 of the body 46. These ribs serve as seals to prevent the flow of conductive jelly or other body secretions or fluids which might otherwise provide short circuits between the electrodes 40, 42 and 44. The use and operation of the electrode structure shown in FIGS. 3 and 4 may be as explained above in connection with FIGS. 1 and 2.

Figure 5:
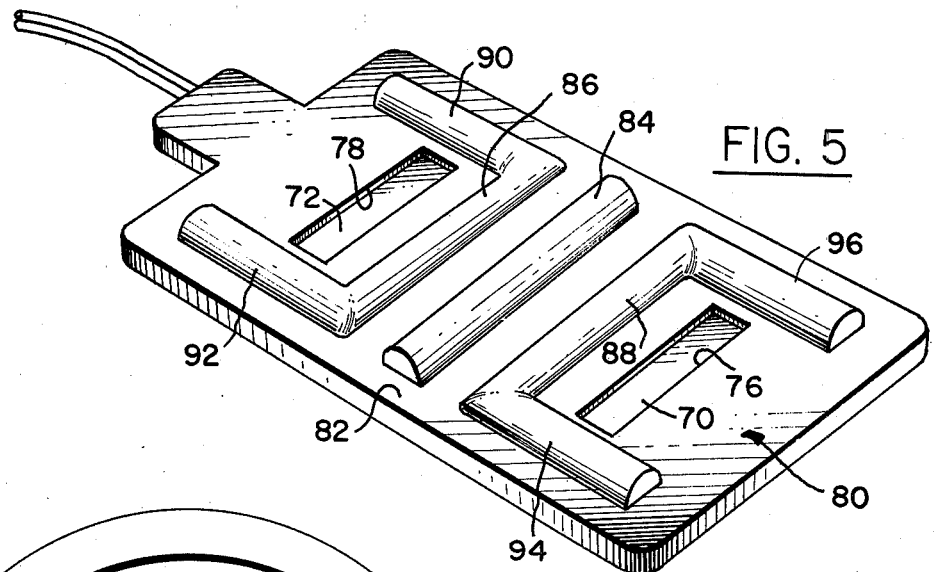
FIG. 5 is a perspective view of an electrode structure in accordance with another embodiment of the invention.

FIG. 5 shows an electrode structure, which similar to FIG. 1, has a pair of electrodes 70 and 72 disposed at the bottom of wells 76 and 78 in a generally rectangular body 80 of flexible non-conductive material. In the region 82 between the wells 76 and 78, there is located a central rib 84 and two additional ribs 86 and 88 which are parallel to the central rib 84. The ribs 86 and 88 have longitudinally extending portions 90, 92, 94 and 96, which extend from the ends thereof. There are thus rib portions 90, 86 and 92, which surround the well 78 on three sides. Three rib portions 94, 88 and 96 surround the other well 76, also on three sides. The electrode structure of FIG. 5, thus provides an arrangement of ribs which when placed in contact with the body surface of the patient provide an effective seal against the flow of body fluids, conductive gel, or the like, between the wells and inhibits any short circuits between the electrodes 70 and 72. The electrode structure shown in FIG. 5 may be molded to form it as an integral device as was explained above in connection with FIGS. 1 and 2. Other than the arrangement of the ribs 84, 86, 88, 90, 92, 94 and 96, the electrode structure of FIGS. 1 and 2 and of FIG. 5 are similar.

Figure 6:
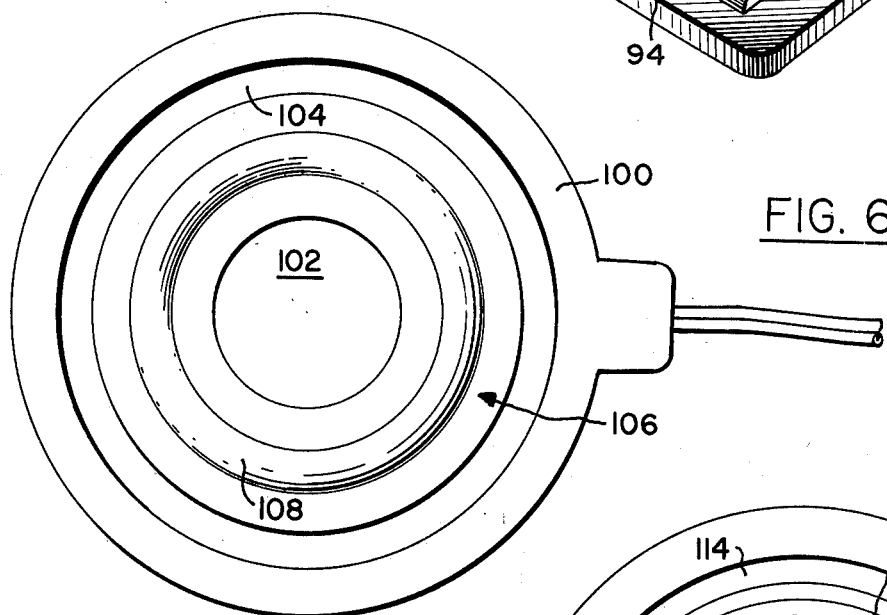
FIG. 6 is a plan view of an electrode structure in accordance with a further embodiment of the invention.

Referring to FIG. 6, there is shown an electrode structure which, in accordance with another embodiment of the invention, is generally circular in shape. A generally circular body of flexible non-conductive material 100 contains the electrode 102 at the center of the body 100. The center electrode 102 is a circular platelet of conductive material, such as conductive rubber. Surrounding the electrode 102 is a ring-shape electrode 104. Both the center electrode 102 and the ring electrode 104 may be disposed at the bottom of wells in the body 100. The well which has the electrode 102 at the bottom thereof is generally cylindrical in shape while the well which has the electrode 104 at the bottom thereof is in the form of a ring or shell. The region 106 between the wells is formed with a circular rib 108. This rib provides a seal when the electrode structure is placed in contact with the skin. Accordingly, conductive jelly or the conductive secretions, or the like, are inhibited from flowing between the electrodes 102 and 104 by the circular seals provided by the rib 108.

Figure 7:
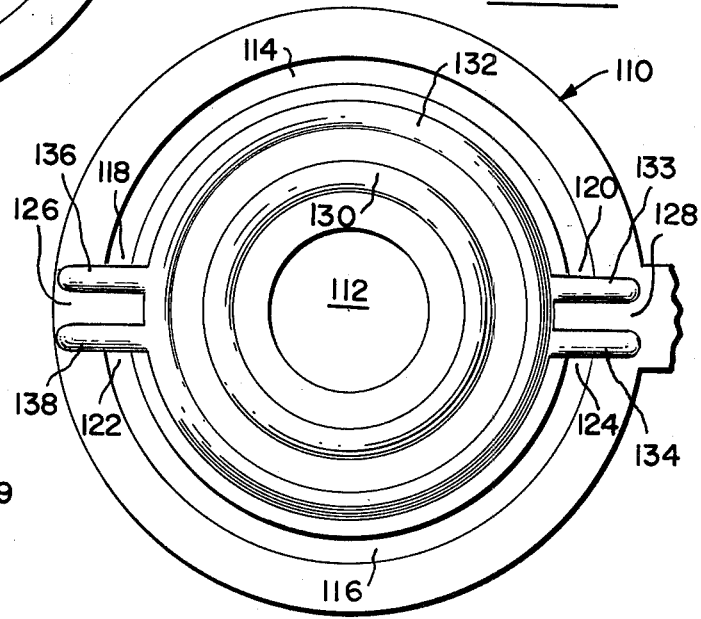
FIG. 7 is a plan view of an electrode structure in accordance with a still further embodiment of the invention.

Referring to FIG. 7, there is shown a circular electrode structure provided by a body of non-conductive material 110. A circular electrode 112 is disposed at the center of the body 110 and is contained therein at the bottom of a well. The arrangement of the electrode 112 and of the electrode 102 in the structure of FIG. 6 are similar. The electrode structure of FIG. 7 has two outer electrodes 114 and 116 which are contained within the body 110. These outer electrodes are conductive platelets which encompass sectors of a circle which are disposed on opposite sides of a diameter of the body 110. In other words, the opposite ends 118 and 120 of the electrode 114 terminate on one side of the diameter while the opposite ends 122 and 124 of the other outer electrode 116 terminate on the opposite side of the diameter. The ends 118 and 120 are spaced from each other, as are the ends 122 and 124. Regions 126 and 128 of the surface of the body 110 separates and insulates the outer electrodes 114 and 116 from each other.

A circular rib 130 surrounds the well in which the central electrode 112 is disposed. A second or outer circular rib 132 of larger diameter than the first rib 130 is also disposed on the body 110. Pairs of ribs 132 and 134 and 136 and 138 extend radially outward from the second or outer circular rib 132 across the regions 126 and 128 which separate the ends 118 and 120 and 122 and 124 of the outer electrodes 114 and 116. This arrangement of ribs 130, 132, 133, 134, 136 and 138 provides for an effective seal against conductive jelly or other body secretions or fluids which might cause short circuits between the electrodes 112, 114 and 116.

Figure 8:
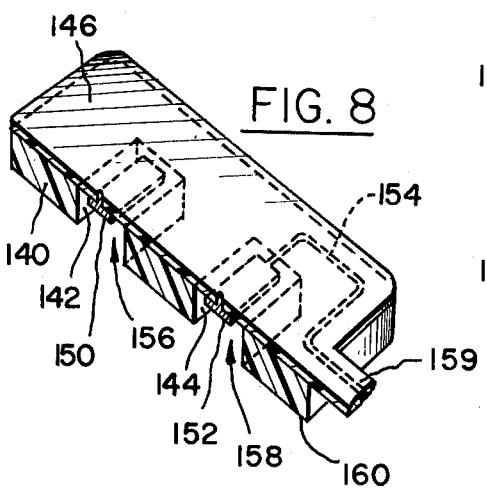
FIG. 8 is a fragmentary sectional view of an electrode structure in accordance with a still further embodiment of the invention.

Referring to FIG. 8, there is shown still another electrode structure embodying the invention. There is provided a two part body of flexible non-conductive material in the electrode structure of FIG. 8. One of these parts 140 is a generally rectangular piece of flexible plastic foam. A suitable flexible plastic foam is a closed cell polyethylene foam. The part 140 is formed with rectangular holes 142 and 144 therein. The other part of the flexible conductive body is the base board of a flexible printed circuit board 146. The conductive pads 150 and 152 which may be plated, are printed on the side of the board 146 which is attached to the body 140 of flexible plastic foam. The plating is preferably silver which is chlorided after being plated. The remainder of the clad surface of the board 146, which carries the printed electrodes and their connections, is preferably coated with insulating material. Attachment of the board 146 to the body 140 may be made by means of cement or by laminating. The body of plastic foam may be made from flexible tape which is coated with adhesive on both sides. The tape is of plastic foam material. A suitable tape is MED 416, available commercially from Fasson Corp. of Painesville, Ohio. Printed conductors are also located on the board 146. The conductor 154 which is extended to the pad 152 is illustrated in FIG. 8. Another similar conductor which may extend along the opposite side of the board is provided for connection to the conductor pad 150. The board 146 may be provided with a tail 159 which may be 2 or 3 inches long. The conductor 154 and any other conductors extend along the tail. The end of the tail may be provided with printed circuit edge connectors to which the conductors 154 are connected. The tail may be corrugated to enhance its flexibility.

When the body 140 and the board 146 are attached to each other, the conductive pads 150 and 152 are disposed in registry with the openings 142 and 144. The openings 142 and 144 thus form blind holes in the electrode structure. These blind holes provide wells 156 and 158. The wells may be used to receive conductive jelly when the electrode structure is disposed in operative position with the free face 160 of the body 140 placed against the skin of the patient. In the event the board 146 is very thin, a backing sheet (not shown) may be laminated thereto to increase its strength without sacrificing flexibility. The printed circuit board 146 can be made by silk screening conductive ink onto an inexpensive substrate such as vinyl or coated paper and used with the double sided adhesive foam body 140. The board is attached through a connector to the instrument cable. This makes the electrode structure even more inexpensive and disposable.

Tacky material may be coated on the surface 160 for adhering the electrode structure to the skin. One or more ribs (not shown) may be provided in the region between the wells 156 and 158. These ribs will extend laterally across the electrode structure and project outwardly from the face 160.

From the foregoing description, it will be apparent that there has been provided improved electrode structures for deriving electrical signals representing physiological activity. The electrode structures herein described are especially suitable for use with electromyographic instruments. These structures are very low in cost and may for example be thrown away after use, as a matter of convenience or for sanitary reasons. While several embodiments of the electrode structure provided by the invention have been described, variations and modifications therein within the scope of the invention will undoubtedly suggest themselves to those skilled in the art.

Accordingly, the foregoing description should be taken merely as illustrative and not in any limiting sense.

What is claimed is:

1. For use with apparatus for deriving electrical signals associated with physiological activity, an electrode structure for deriving said signals when disposed upon a body surface, said electrode structure comprising a unitary body of moldable, flexible, soft, elastic, non-conductive material having faces on opposite sides thereof, one face of said opposite faces adapted to be disposed in contact with said body surface, said unitary body having at least one blind opening which extends therein from said one face and forms at least one well therein, an electrode member of flexible, soft, elastic material similar to the material of said unitary body disposed within said unitary body at the bottom of said well, said well being adapted to receive conductive jelly which is disposed in contact with said electrode member, and conductor means connected to the said electrode member for carrying said signals from said electrode member to said apparatus.

2. The invention as set forth in claim 1 wherein said unitary body has a plurality of said blind openings therein which forms a plurality of said wells in spaced relationship along said body, adjacent pairs of said wells each being separated by a region of said unitary body, each of said wells having separate electrode members at the bottom thereof, said conductor means providing connections separately to each of said electrode members, each of said wells being adapted to receive said conductive jelly in contact with said electrode members therein.

3. The invention as set forth in claim 2 wherein said region of said body has at least one rib formed of said material and as a unitary part of said unitary body and projecting away from said one face, and disposed to separate the wells of each of said adjacent pairs of wells, said rib being of a size to define a seal with said body surface when said one face is in contact therewith to inhibit the flow of said jelly between said wells across said region.

4. The invention as set forth in claim 3 wherein said region has a plurality of said ribs in side by side relationship between said wells.

5. The invention as set forth in claim 3 wherein said body consists of polymeric material of the class consisting of natural and silicone rubber and polyurethane.

6. The invention as set forth in claim 5 wherein the material of said electrode members contains polymeric material and conductive material and is of the class of materials including conductive rubber.

7. The invention as set forth in claim 3 wherein said one face of said body which is adapted to be disposed in contact with said body surface is of generally rectangular shape, said wells being spaced of and from each other longitudinally of said body, and said rib extending laterally across said one face with the ends of said rib extending past the sides of said wells which are closest to the longitudinal edges of said one face.

8. The invention as set forth in claim 7 wherein the ends of said rib are coterminous with the longitudinal edges of said one face.

9. The invention as set forth in claim 7 wherein a plurality of said laterally extending ribs are disposed across said region, the ones of said ribs adjacent said wells having legs, extending from the opposite ends of said lateral ribs in a longitudinal direction between the sides of said wells and the longitudinal edges of said one face.

10. The invention as set forth in claim 3 wherein said one face of said body which is adapted to be disposed in contact with said body surface is of generally circular shape, said wells having a first circular well disposed at the center of said face and a second well of ring shape around said first well, a circular electrode member at the bottom of said first well and a ring shaped electrode member at the bottom of said second well, said region including the annular space between said first well and said second well, and said rib being of circular shape and being disposed in said region.

11. The invention as set forth in claim 10 wherein said second well has two parts each on opposite sides of a diameter of said circular face of said body so as to divide said second well into two parts, separate electrode members at the bottom of each of said second well parts and said circular rib having rib extensions disposed parallel to said diameter and between the ends of said second well parts.

* * * * *